(12) United States Patent
Chini et al.

(10) Patent No.: US 8,431,131 B2
(45) Date of Patent: Apr. 30, 2013

(54) CD38 AND OBESITY

(75) Inventors: Eduardo N. Chini, Rochester, MN (US); Maria Thereza P. Barbosa, Rochester, MN (US); Sandra M. Soares Herrmann, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/398,721

(22) Filed: Feb. 16, 2012

(65) Prior Publication Data

US 2012/0207768 A1 Aug. 16, 2012

Related U.S. Application Data

(62) Division of application No. 12/244,546, filed on Oct. 2, 2008, now Pat. No. 8,143, 014.

(60) Provisional application No. 60/977,008, filed on Oct. 2, 2007.

(51) Int. Cl.
*A61K 39/395* (2006.01)
*C07K 16/28* (2006.01)
*C07K 16/40* (2006.01)

(52) U.S. Cl.
USPC .................. 424/172.1; 530/387.1; 514/909

(58) Field of Classification Search .................. None
See application file for complete search history.

(56) References Cited

U.S. PATENT DOCUMENTS

| | | | |
|---|---|---|---|
| 6,576,660 B1 * | 6/2003 | Liao et al. ...................... | 514/456 |
| 7,829,673 B2 * | 11/2010 | De Weers et al. .......... | 530/387.1 |
| 2006/0223884 A1 | 10/2006 | Chapal et al. | |
| 2006/0292652 A1 | 12/2006 | Curtis et al. | |

OTHER PUBLICATIONS

Barbosa et al. The enzyme CD38 (a NAD glycohydrolase, EC 3.2.2. 5) is necessary for the development of diet-induced obesity. FASEB J. Nov. 2007;21(13):3629-39. Epub Jun. 21, 2007.*
Kellenberger et al. Flavonoids as inhibitors of human CD38. Bioorg Med Chem Lett. Jul. 1, 2011;21(13):3939-42. Epub May 14, 2011.*
Hirsch J. The search for new ways to treat obesity. Proc Natl Acad Sci U S A. Jul. 9, 2002;99(14):9096-7.*
Woods et al. Signals that regulate food intake and energy homeostasis. Science. May 29, 1998;280(5368):1378-83.*
"Gene Deficiency is a Protective Barrier to Obesity" [online]. Mayo Clinic, 2007, [retrieved on Oct. 10, 2008]. Retrieved from the Internet: <URL: http://www.eurekalert.org/pub_releases/2007-06/mc-gdi062607.php>.
Aksoy et al., "Regulation of intracellular levels of NAD: A novel role for CD38," *Biochem. Biophys. Res. Commun.*, 2006, 345:1386-1392.
Aksoy et al., "Regulation of SIRT 1 mediated NAD dependent deacetylation: A novel role for the multifunctional enzyme CD38," *Biochem. Biophys. Res. Commun.*, 2006, 349:353-359.

Barbosa et al., "The enzyme CD38 (a NAD glycohydrolase, EC 3.2.2.5) is necessary for the development of diet-induced obesity," *FASEB J.*, 2007, 21:3629-3639.
Baines and Thorpe, "Purification of Immunoglobulin G (IgG)," *Meth. Mol. Biol.*, 1992, 10:79-104.
Baur et al., "Resveratrol improves health and survival of mice on a high-calorie diet," *Nature*, 2006, 444:337-342.
Chini, "Interactions between intracellular $Ca^{2+}$ stores: $Ca^{2+}$ eleased from the NAADP pool potentiates cADPR-induced $Ca^{2+}$ release," *Braz. J. Med. Biol. Res.*, 2002, 35:543-547.
Coligan et al., "Production of Polyclonal Antisera in Rabbits, Rats, Mice and Hamsters," *Current Protocols In Immunology*, 1992, sections 2.4.1, 2.5.1, 2.6.7, 2.7.1, 2.7.12, 2.9.1 and 2.9.3.
Coligan et al., *Current Protocols In Immunology*, 1994, Unit 9, Wiley Interscience.
El-Deiry et al., "Definition of a consensus binding site for p53," *Nat. Genet.*, 1992, 1:45-49.
Fernandez-Zapico et al., "An mSin3A interaction domain links the transcriptional activity of KLF11 with its role in growth regulation," *EMBO J.*, 2003, 22(18):4748-4758.
Folch et al., "A simple method for the isolation and purification of total lipides from animal tissues," *J. Biol. Chem.*, 1957, 226:497-509.
Galione and Churchill, "Cyclic ADP Ribose as a Calcium-Mobilizing Messenger," *Sci. STKE.*, 2000, 41:PE1.
Green et al., "Production of Polyclonal Antisera," *Immunochemical Protocols*, 1992, Manson.(ed.), Humana Press, pp. 1-5.
Harlow et al., *Antibodies: A Laboratory Manual*, 1988, Cold Spring Harbor Pub., p. 726.
Johnson et al., "Suppressed insulin signaling and increased apoptosis in CD38-null islets," *Diabetes*, 2006, 55:2737-2746.
Köhler and Milstein, "Continuous cultures of fused cells secreting antibody of predefined specificity," *Nature*, 1975, 256:495-497.
Lagouge et al., "Resveratrol improves mitochondrial function and protects against metabolic disease by activating SIRT1 and PGC-1α," *Cell*, 2006, 127:1109-1122.
Macleod et al., "p53-dependent and independent expression of p21 during cell growth, differentiation, and DNA damage," *Genes Dev.*, 1995, 9:935-944.
Novak et al., "Neuromedin U in the paraventricular and arcuate hypothalamic nuclei increases non-exercise activity thermogenesis," *J. Neuroendocrinol.*, 2006, 18:594-601.
Partida-Sánchez et al., "Cyclic ADP-ribose production by CD38 regulates intracellular calcium release, extracellular calcium influx and chemotaxis in neutrophils and is required for bacterial clearance in vivo," *Nat. Med.*, 2001, 7(11):1209-1216.
Puigserver, "Tissue-specific regulation of metabolic pathways through the transcriptional coactivator PGC1-α," *Intl. J. Obesity*, 2005, 29:S5-S9.
Rodgers et al., "Nutrient control of glucose homeostasis through a complex of PGC-1α and SIRT1," *Nature*, 2005, 434:113-118.
Takasawa et al., "Cyclic ADP-ribose and inositol 1,4,5-trisphosphate as alternate second messengers for intracellular $Ca^{2+}$ mobilization in normal and diabetic β-cells," *J. Biol. Chem.*, 1998, 273(5):2497-2500.
Thompson et al., "Role of CD38 in myometrial $Ca^{2+}$ transients: modulation by progesterone," *Am. J. Physiol. Endocrinol. Metab.*, 2004, 287:E1142-E1148.

* cited by examiner

*Primary Examiner* — David Romeo
(74) *Attorney, Agent, or Firm* — Fish & Richardson P.C.

(57) ABSTRACT

This document provides methods and materials relating to obesity. For example, methods and materials related to treating obesity and identifying agents having the ability to treat obesity are provided.

5 Claims, 13 Drawing Sheets

CD38 AND OBESITY

CROSS-REFERENCE TO RELATED APPLICATIONS

This application is a divisional of U.S. application Ser. No. 12/244,546, filed Oct. 2, 2008, which claims the benefit of U.S. Provisional Application Ser. No. 60/977,008, filed on Oct. 2, 2007. The disclosures of the prior applications are considered part of (and are incorporated by reference in) the disclosure of this application.

BACKGROUND

1. Technical Field

This document provides methods and materials relating to obesity. For example, this document relates to methods and materials involved in treating obesity and identifying agents having the ability to treat obesity.

2. Background Information

Obesity is increasingly viewed as a serious and growing public health problem. In fact, excessive body weight can predispose a mammal to various diseases such as cardiovascular diseases, diabetes mellitus type 2, sleep apnea, and osteoarthritis. Elucidating the signaling mechanisms by which high fat caloric diet induces obesity can help provide a better understanding of this condition.

SUMMARY

This document provides methods and materials relating to obesity. For example, this document provides methods and materials related to treating obesity and identifying agents having the ability to treat obesity.

In general, one aspect of this document features a method for treating a mammal having an obesity condition or suspected to develop the obesity condition. The method comprises administering, to the mammal, an inhibitor of CD38. The mammal can be a human. The mammal can be obese. The inhibitor can be administered to the mammal under conditions wherein a symptom of the obesity improves. The obesity can improve by at least 25 percent. The inhibitor can be an anti-CD38 antibody.

Another aspect of this document features a method for identifying a treatment agent for treating obesity. The method comprises (a) determining whether or not a test agent inhibits CD38, wherein inhibition of CD38 indicates that the test agent is a candidate agent, and (b) administering the candidate agent to a mammal to determine whether or not the candidate agent reduce the weight of the mammal or reduce weight gain in the mammal, wherein a reduction is the weight or weight gain indicates that the candidate agent is the treatment agent. Step (a) can comprise using an in vitro CD38 activity assay. The mammal can be a mouse.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
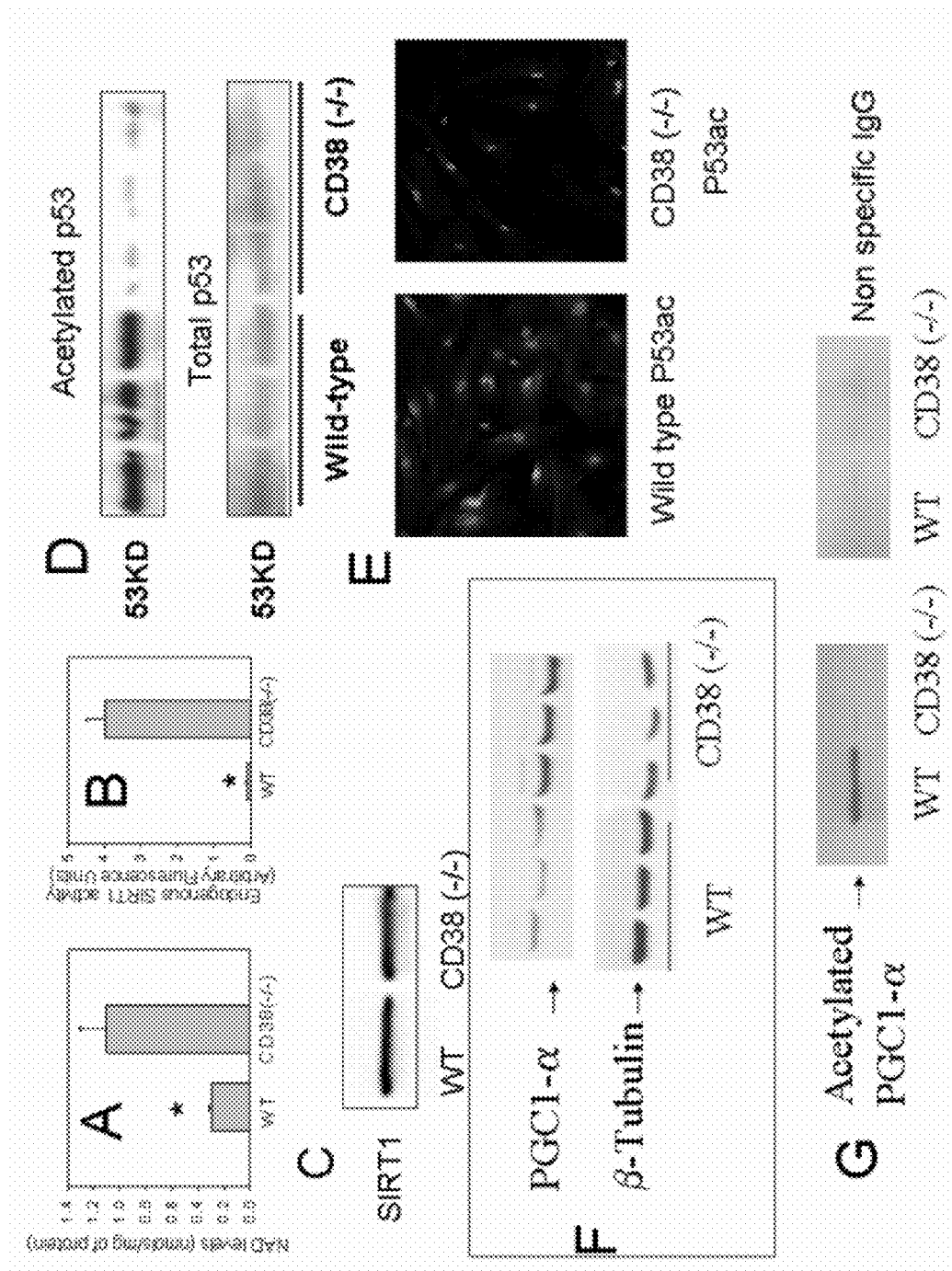
FIG. 1. CD38 regulates NAD levels, SIRT activity, and PGC1α levels. In A-C, NAD levels, endogenous nuclear SIRT activity, and SIRT levels were determined in muscle from wild type and CD38 (−/−) mice. In D, total and acetylated P53 were determined in brain homogenates from wild type and CD38 (−/−), each lane represents one independent animal. In E, cultured smooth muscle cells were fixed and assayed for acetylated P53 (green staining) Propidium iodide (PI) stain was used as a control (red staining) In F, PGC1α levels were detected by western blot. Tubulin was used as a loading control. In G, acetylated PGC1α levels were detected by western blot. Non-specific IgG was used as a control. Each lane represents a sample from one independent animal. All experiments were repeated at least 3-8 times. The asterisk denotes significant difference $p<0.05$.

This document provides methods and materials relating to obesity. For example, this document provides methods and materials related to treating obesity and identifying agents having the ability to treat obesity.

In some cases, an inhibitor of CD38 can be used to treat obesity in a mammal. The mammal can be any type of mammal including, without limitation, a mouse, rat, dog, cat, horse, sheep, goat, cow, pig, monkey, or human. An inhibitor of CD38 can be any agent that reduces CD38 expression (e.g., an siRNA molecule, antisense oligonucleotide, or peptide nucleic acid) or CD38 activity (e.g., an inhibitory anti-CD38 antibody or CD38 antagonist such as nicotinamide or nicotinic acid). An antibody can be, without limitation, a polyclonal, monoclonal, human, humanized, chimeric, or single-chain antibody, or an antibody fragment having binding activity, such as a Fab fragment, F(ab') fragment, Fd fragment, fragment produced by a Fab expression library, fragment comprising a VL or VH domain, or epitope binding fragment of any of the above. An antibody can be of any type (e.g., IgG, IgM, IgD, IgA or IgY), class (e.g., IgG1, IgG4, or IgA2), or subclass. In addition, an antibody can be from any animal including birds and mammals. For example, an antibody can be a human, rabbit, sheep, or goat antibody. An antibody can be naturally occurring, recombinant, or synthetic. Antibodies can be generated and purified using any suitable methods known in the art. For example, monoclonal antibodies can be prepared using hybridoma, recombinant, or phage display technology, or a combination of such techniques. In some cases, antibody fragments can be produced synthetically or recombinantly from a gene encoding the partial antibody sequence. An anti-CD38 antibody can bind to a CD38 polypeptide at an affinity of at least $10^4$ mol$^{-1}$ (e.g., at least $10^5$, $10^6$, $10^7$, $10^8$, $10^9$, $10^{10}$, $10^{11}$, or $10^{12}$ mol$^{-1}$).

An anti-CD38 antibody provided herein can be prepared using any appropriate method. For example, any substantially pure CD38 polypeptide, or fragment thereof (e.g., a truncated CD38 polypeptide), can be used as an immunogen to elicit an immune response in an animal such that specific antibodies are produced. Thus, a human CD38 polypeptide or a fragment thereof can be used as an immunizing antigen. In addition, the immunogen used to immunize an animal can be chemically synthesized or derived from translated cDNA. Further, the immunogen can be conjugated to a carrier polypeptide, if desired. Commonly used carriers that are chemically coupled to an immunizing polypeptide include, without limitation, keyhole limpet hemocyanin (KLH), thyroglobulin, bovine serum albumin (BSA), and tetanus toxoid.

The preparation of polyclonal antibodies is well-known to those skilled in the art. See, e.g., Green et al., Production of Polyclonal Antisera, in IMMUNOCHEMICAL PROTOCOLS (Manson, ed.), pages 1-5 (Humana Press 1992) and Coligan et al., Production of Polyclonal Antisera in Rabbits, Rats, Mice and Hamsters, in CURRENT PROTOCOLS IN IMMUNOLOGY, section 2.4.1 (1992). In addition, those of skill in the art will know of various techniques common in the immunology arts for purification and concentration of polyclonal antibodies, as well as monoclonal antibodies (Coligan, et al., Unit 9, CURRENT PROTOCOLS IN IMMUNOLOGY, Wiley Interscience, 1994).

The preparation of monoclonal antibodies also is well-known to those skilled in the art. See, e.g., Kohler & Milstein, Nature 256:495 (1975); Coligan et al., sections 2.5.1 2.6.7; and Harlow et al., ANTIBODIES: A LABORATORY MANUAL, page 726 (Cold Spring Harbor Pub. 1988). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well established techniques. Such isolation techniques include affinity chromatography with Protein A Sepharose, size exclusion chromatography, and ion exchange chromatography. See, e.g., Coligan et al., sections 2.7.1 2.7.12 and sections 2.9.1 2.9.3; Barnes et al., Purification of Immunoglobulin G (IgG), in METHODS IN MOLECULAR BIOLOGY, Vol. 10, pages 79-104 (Humana Press 1992).

Once hybridoma clones that produce antibodies to an antigen of interest (e.g., a CD38 polypeptide) have been selected, further selection can be performed for clones that produce antibodies having a particular specificity. For example, clones can be selected that produce antibodies that preferentially bind to a CD38 polypeptide and inhibit CD38 polypeptide activity.

The antibodies provided herein can be substantially pure. The term "substantially pure" as used herein with reference to an antibody means the antibody is substantially free of other polypeptides, lipids, carbohydrates, and nucleic acid with which it is naturally associated in nature. Thus, a substantially pure antibody is any antibody that is removed from its natural environment and is at least 60 percent pure. A substantially pure antibody can be at least about 65, 70, 75, 80, 85, 90, 95, or 99 percent pure.

This document also provides methods and materials related to treating mammals (e.g., humans) likely to develop obesity (e.g., mammals having an elevated risk of developing diet-induced obesity). A mammal can be identified as having or being likely to develop obesity using standard clinical techniques. For example, analysis of a human's family history or eating habits can be used to determine whether or not the human is likely to develop an obesity condition. As described herein, a mammal identified as having or being susceptible to developing an obesity condition can be treated by administering an inhibitor of CD38.

Agents that can inhibit CD38 expression or activity in cells can be identified by screening candidate agents (e.g., from synthetic compound libraries and/or natural product libraries). Candidate agents can be obtained from any commercial source and can be chemically synthesized using methods that are known to those of skill in the art. Candidate agents can be screened and characterized using in vitro cell-based assays, cell free assays, and/or in vivo animal models. For example, a CD38 NADase assay can be used to identify CD38 antagonists. NADase activity can be determined using etheno-NAD. Enzyme preparations (e.g., purified CD38) can be incubated in a medium containing, for example, 0.2 mM NGD, 0.25 M sucrose, and 40 mM Tris-HCl (pH 7.2) at 37° C. NADase activity can be determined by measuring the change in fluorescence over time at, for example, 300 nm excitation and 410 nm emission. Candidate agents can be added to the CD38 assay, and a decrease of the NADase activity compared to control can be determined. A reduction in NADase activity can indicate that the candidate agent is a CD38 antagonist and can be used to treat obesity as described herein.

An inhibitor of CD38 can be administered to a mammal alone or in combination with other agents such as another inhibitor of CD38. For example, a composition containing an anti-CD38 antibody can be administered to a mammal in need of treatment for an obesity condition. Such a composition can contain additional ingredients including, without limitation, pharmaceutically acceptable vehicles. A pharmaceutically acceptable vehicle can be, for example, saline, water, lactic acid, or mannitol.

A composition containing an inhibitor of CD38 can be administered to mammals by any appropriate route, such as enterally (e.g., orally), parenterally (e.g., subcutaneously, intravenously, intradermally, intramuscularly, or intraperitoneally), intracerebrally (e.g., intraventricularly, intrathecally, or intracisternally) or intranasally (e.g., by intranasal inhalation).

Suitable formulations for oral administration can include tablets or capsules prepared by conventional means with pharmaceutically acceptable excipients such as binding agents (e.g., pregelatinized maize starch, polyvinylpyrrolidone or hydroxypropyl methylcellulose), fillers (e.g., lactose, microcrystalline cellulose or calcium hydrogen phosphate), lubricants (e.g., magnesium stearate, talc or silica), disintegrants (e.g., potato starch or sodium starch glycolate), or wetting agents (e.g., sodium lauryl sulfate). Tablets can be coated by methods known in the art. Preparations for oral administration can also be formulated to give controlled release of the agent.

Intranasal preparations can be presented in a liquid form (e.g., nasal drops or aerosols) or as a dry product (e.g., a powder). Both liquid and dry nasal preparations can be administered using a suitable inhalation device. Nebulized aqueous suspensions or solutions can also be prepared with or without a suitable pH and/or tonicity adjustment.

A composition containing an inhibitor of CD38 can be administered to a mammal in any amount, at any frequency, and for any duration effective to achieve a desired outcome (e.g., to reduce a mammal's weight). In some cases, a composition containing an inhibitor of CD38 can be administered to a mammal to reduce a mammal's weight by 1, 5, 10, 11, 12, 13, 14, 15, 16, 17, 18, 19, 20, 25, 30, 35, 40, 45, 50, 55, 60, 65, 70 percent or more). An effective amount of an inhibitor of CD38 can be any amount that reduces a mammal's weight without producing significant toxicity to a mammal. Typically, an effective amount of an inhibitor of CD38 can be any amount greater than or equal to about 10 μg provided that that amount does not induce significant toxicity to the mammal upon administration. In some cases, an effective amount of an inhibitor of CD38 can be between 1 μg and 500 mg (e.g., between 1 µg and 250 mg, between 1 µg and 200 mg, between 1 µg and 150 mg, between 1 µg and 100 mg, between 1 µg and 50 mg, between 1 µg and 10 mg, between 1 µg and 1 mg, between 1 µg and 100 µg, between 1 µg and 50 µg, between 5 µg and 100 mg, between 10 µg and 100 mg, between 100 µg and 100 mg, or between 10 µg and 10 mg). Various factors can influence the actual effective amount used for a particular application. For example, the frequency of administration, duration of treatment, use of multiple treatment agents, route of administration, and severity of the obesity may require an increase or decrease in the actual effective amount administered.

The frequency of administration of an inhibitor of CD38 can be any frequency that reduces a mammal's weight without producing significant toxicity to the mammal. For example, the frequency of administration can be from about three times a day to about twice a month, or from about once a week to about once a month, or from about once every other day to about once a week, or from about once a month to twice a year, or from about four times a year to once every five years, or from about once a year to once in a lifetime. The frequency of administration can remain constant or can be variable during the duration of treatment. For example, an inhibitor of CD38 can be administered daily, twice a day, five days a week, or three days a week. An inhibitor of CD38 can be administered for five days, 10 days, three weeks, four weeks, eight weeks, 48 weeks, one year, 18 months, two years, three years, or five years. A course of treatment can include rest periods. For example, an inhibitor of CD38 can be administered for five days followed by a nine-day rest period, and such a regimen can be repeated multiple times. As with the effective amount, various factors can influence the actual frequency of administration used for a particular application. For example, the effective amount, duration of treatment, use of multiple treatment agents, route of administration, and severity of the obesity may require an increase or decrease in administration frequency.

An effective duration for administering an inhibitor of CD38 can be any duration that reduces a mammal's weight without producing significant toxicity to the mammal. Thus, the effective duration can vary from several days to several weeks, months, or years. In general, the effective duration for the treatment of obesity can range in duration from several days to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the obesity.

This document also provides methods and materials for identifying agents that can be used to treat a mammal having or being likely to develop an obesity disorder. For example, a CD38 activity assay (e.g., a CD38 NADase assay) can be used to identify agents that can be used to treat a mammal having or being likely to develop an obesity disorder. In addition, an animal model resistant to diet-induced obesity (e.g., CD38 knockout mice) can be used as a control for confirming an agents ability to treat obesity.

The invention will be further described in the following examples, which do not limit the scope of the invention described in the claims.

EXAMPLES

Example 1

CD38 (an NAD glycohydrolase, E.C. 3.2.2.5) is necessary for the development of diet-induced obesity CD38 Wild-Type and Knockout Mice Wild-type and CD38 knockout mice (C57BL/6J.129 CD38$^{-/-}$, N12 backcross) similar to those described elsewhere (Partida-Sanchez et al., *Nat. Med.*, 7:1209-1216 (2001) and Takasawa et al., *J. Biol. Chem.*, 273:2497-2500 (1998)) were obtained and maintained in a breeding facility in accordance with all animal care guidelines.

Metabolic Studies and Diet At one year of age, CD38 (−/−) mice were placed on either a normal caloric diet (NCD; diet number 3807, KLIBA-NAFAG) or an HFD (AIN-93G modified to provide 60% of calories from fat, Researchdiets) ad libitum and monitored for six weeks. Body weight was recorded weekly, and food intake was measured for seven consecutive days. Oxygen consumption and energy expenditure (ER) measurements were performed in mice fed HFD for four weeks, and quantification of blood metabolites were performed. For the experiments using resveratrol and sirtinol, the HFD was supplemented with daily intraperitoneal injections of 30 mg/kg of drug (or vehicle) for two weeks.

Cultured Smooth Muscle Cells from Wild-Type and CD38 Knockout Mice

Smooth muscle cells were isolated using techniques described elsewhere (Thompson et al., *Am. J. Physiol. Endocrinol. Metab.*, 287:E1142-1148 (2004)). Myometrium was minced in Hanks' balanced salt solution (HBSS) containing 10 mM glucose and 10 mM HEPES (pH 7.4). The tissue was then suspended in fresh HBSS, aerated with 95% $O_2$-5% $CO_2$, and incubated in a 37° C. water bath with gentle shaking for two hours in the presence of 20 U/mL papain and 2,000 U/mL DNase. Subsequently, the tissue was incubated for an additional two hours at 37° C., with the addition of 1 mg/mL type IV collagenase. Myometrial cells were released by trituration, centrifuged, and suspended in Smooth Muscle Cell Basal Medium (SmBM, Clonetics CC 3181) containing 5% FCS, 100 U/L penicillin, 100 µg/L streptomycin, 0.25 µg/L amphotericin B, 0.05 mg/mL insulin, and 5 ng/mL human EGF. Cultures were grown and maintained in 75-cm$^2$ plastic flasks in a humidified incubator supplied with 5% $CO_2$-95% air at 37° C. Subcultures were obtained as needed by detaching the cells with a $Ca^{2+}$/$Mg^{2+}$-free HBSS solution containing 0.25% trypsin and 5 mM EDTA. Only cultures between passages two and ten were used. Cells isolated by this procedure stain positive for smooth muscle actin and negative for keratin.

For experiments, cells were made quiescent by replacing the growth medium with SmBM without serum or growth factors. Cell medium was again replaced with SmBM containing testing agents solubilized in 0.1% DMSO or water added to the final concentrations.

Western Blot for P53 and SIRT1

Liver, brain, heart, and skeletal muscle tissues were surgically removed from wild-type and CD38 knockout mice, washed three times in ice-cold HBSS, and homogenized in 40 mM Tris-HCl (pH 7.4) containing 0.25 M sucrose using a Dounce homogenizer. Homogenates from smooth muscle cells in culture were prepare by scraping the cells in the presence of homogenizing buffer. The homogenates were centrifuged at 10,000 g for 10 minutes, and the resultant supernatant assayed for protein using the DC protein assay (Bio-Rad, Hercules, Calif.). The lysates (1000 µL) were adjusted to contain 1 mg protein and 10 µg mouse monoclonal anti-p53 antibody conjugated to agarose beads (Santa Cruz Biotechnology, Santa Cruz, Calif.) added overnight at 4° C. with gentle rocking. The antibody-polypeptide complex was centrifuged at 1000 g for two minutes, and the pellet was washed four times in sucrose buffer and resuspended in 30 µL of sucrose buffer and 30 µL Laemmli buffer. The supernatants were denatured at 100° C. for three to five minutes, and 50 µL of sample was subjected to SDS-PAGE using the Criterion Gel System (Bio-Rad) and a 4-15% gradient gel. The gels were exposed to a constant current of 200 V for 70 minutes followed by transfer to PVDF membranes (Bio-Rad). The membranes were blocked for one hour in 5% nonfat dried milk in TBS containing 0.1% Tween 20 followed by incubation with anti-acetylated p53 rabbit polyclonal antibody (1:1000) (Abcam, Inc., Cambridge, Mass.) overnight at 4° C. with gentle rocking. The membrane was then probed with an HRP-conjugated donkey anti-rabbit antibody (1:10,000) (Santa Cruz Biotechnology) for one hour at room temperature. Blots were visualized by exposing them to BioMax MR film (Eastman Kodak Co, Rochester, N.Y.) using Supersignal Substrate (Pierce Biotechnology, Inc., Rockford, Ill.). Western blot for an SIRT1 polypeptide was performed using a SIRT1 specific antibody from Upstate Biotechnology (Charlottesville, Va.).

Immuno-Staining for Acetylated P53 Using Confocal Microscopy

Smooth muscle cells were obtained as described above. Cells were fixed in suspension in PBS plus 2% paraformaldehyde for 20 minutes at room temperature with constant agitation, and cells were washed three times for 10 minutes with TBS-Triton X-100 (0.1%). After that, cells were incubated in blocking buffer (TBS, 30 mM glycine, and 5% BSA) for 60 minutes and incubated with anti-acetylated p53 rabbit polyclonal antibody (1:1000) (Abcam, Inc.; Cambridge, Mass.) overnight at 4° C. with constant agitation. Primary antibody was removed, and cells were washed three times for 10 minutes with TBS-T. Finally, cells were incubated for one hour with secondary antibody (donkey anti-rabbit antibody; Molecular Probes) in blocking buffer at room temperature.

Laser confocal images were obtained using the Olympus Fluoview laser scanning confocal microscopy, with objective Olympus UplanApo oil, 100×, 1.35 numerical aperture. Nuclei were excited at 543 nm, and their emission recorded at 570 nm.

SIRT1 Polypeptide Activity

SIRT1 polypeptide activity was determined using the SIRT1 Fluorimetric Kit (Biomol International, LP; Plymouth Meeting, Pa.) according to the manufacturer's instructions. Briefly, nuclei prepared from wild-type or CD38 knockout mice (1 µg protein/well) were incubated in 40 mM Tris-HCl (pH 7.4) containing human recombinant SIRT1 (1 U/assay), 500 µM NAD+, and 100 µM Flour de Lys-SIRT1 substrate for 30 minutes at 37° C. Following incubation, the reaction was terminated by addition of a solution containing Flour de Lys Developer and 2 mM nicotinamide. Values were determined by reading fluorescence on a fluorimetric plate reader (Spectramax Gemini XPS; Molecular Devices; Sunnyvale, Calif.) with an excitation wavelength of 360 nm and emitted wavelength of 460 nm. Calculation of net fluorescence expressed as percent of control included the subtraction of a blank consisting of buffer containing no NAD+. Endogenous SIRT polypeptide activity was determined as described above with the exception that no recombinant SIRT enzyme was added to the reaction mixture and that the nuclear preparations were sonicated before the assay. The data were expressed as NAD stimulated deacetylation. No deacetylation was observed in the absence of NAD in nuclei from both wild-type and CD38 knockout mice.

Nuclei Isolation

Mouse nuclei were isolated as described elsewhere (Aksoy et al., *Biochem. Biophys. Res. Commun.*, 349:353-359 (2006)) with minor modifications. The steps of the preparation were performed at 4° C. The Tissues were excised and washed five times with 20 mL ice-cold TKM solution (50 mM Tris-HCl, pH 7.4, 25 mM KCl, and 5 mM $MgCl_2$) to remove blood cells. Tissues were then cut into small pieces and thoroughly homogenized (10 strokes) in 5.0 mL TKM solution supplemented with 0.25 M sucrose (homogenizing medium) using a Dounce homogenizer. The homogenate was filtered through three layers of cheesecloth and centrifuged at 800 g for 10 minutes. The pellet was homogenized in the same volume of medium (five strokes) and centrifuged again at 800 g for 10 minutes. The resulting pellet was re-suspended in 1.0 mL of medium (five strokes) and added to the top of a sucrose gradient containing (from top to bottom) 0.5 mL each of TKM solution with the following concentrations of sucrose, respectively: 1.0, 1.5, and 2.1 M. The tubes were centrifuged in an SW 55 Beckman rotor at 70,000 g for 60 minutes. The resulting pellet was re-suspended in homogenizing medium and centrifuged at 800 g for 10 minutes. The final pellet containing the purified nuclei was re-suspended in homogenizing medium (five strokes) at a protein concentration of 2.5 mg/mL and stored at −70° C. until used. Protein concentration was determined using the Dc protein assay (Bio-Rad, Hercules, Calif.). The purity of nuclear preparations was determined as described elsewhere (Aksoy et al., *Biochem. Biophys. Res. Commun.*, 349:353-359 (2006)). Nuclear preps were found to be nearly 100% pure.

Chromatin Immunoprecipitation Assay (ChIP)

ChIP was performed in cultured smooth muscle cells as described elsewhere (Fernandez-Zapico et al., *EMBO J.* 22:4748-58 (2003)). Briefly, cells from wild type and CD38 knockout animals were cross-linked with formaldehyde for 20 minutes at 25° C., harvested in SDS-lysis buffer (Upstate Biotechnology, Lake Placid, N.Y.), and sheared to fragment DNA (about 500 bp). Samples were then immunoprecipitated using an agarose-conjugated anti-p53 antibody (Santa Cruz Biotechnology, Santa Cruz, Calif.) or IgG control together with agarose beads at 4° C. overnight. Following immunoprecipitation, samples were washed and eluted using the Chromatin Immunoprecipitation Kit (Upstate Biotechnology) according to the manufacturer's instructions. Cross-links were removed at 65° C. for 6 hours, and immunoprecipitated DNA was purified using phenol/chloroform extraction and ethanol precipitation. A 260 bp region flanking p53 binding site in the mouse p21 promoter (Macleod et al., *Genes Dev.*, 9:935-44 (1995) and el-Deiry et al., *Nat. Genet.*, 1:45-9 (1992)) was detected in immunoprecipitated samples by PCR. PCR products were visualized on a 2% agarose gel.

ADP-Ribosyl Cyclase and NADase Activity

ADP-ribosyl cyclase polypeptide activity was measured using the NGD technique as described herein, and NADase polypeptide activity was determined using etheno-NAD as described elsewhere (Johnson et al., Diabetes, 55:2737-2746 (2006)). Enzyme preparations were incubated in a medium containing 0.2 mM NGD, 0.25 M sucrose, and 40 mM Tris-HCl (pH 7.2) at 37° C. Activity was determined by measuring the change in fluorescence over time at 300 nm excitation and 410 nm emission.

Cyclic-ADP-Ribose Induced $Ca^{2+}$ Release cADPR-induced $Ca^{2+}$ release was determined in sea urchin egg homogenates using fluo-3 as a $Ca^{2+}$ indicator as described elsewhere (Chini, *Braz. J. Med. Biol. Res.,* 35:543-547 (2002)). Homogenates from *Lytechinus pictus* egg were prepared as described elsewhere (Chini, *Braz. J. Med. Biol. Res.,* 35:543-547 (2002)). Frozen homogenates were thawed in a 17° C. water bath and diluted to 1.25% with an intracellular medium containing 250 mM N-methyl glutamine, 250 mM potassium gluconate, 20 mM HEPES buffer, pH 7.2, 1 mM $MgCl_2$, 2 U/mL creatine kinase, 4 mM phosphocreatine, 1 mM ATP, 3 µg/mL oligomycin, and 3 µg/mL antimycin. After incubation at 17° C. for 3 hours, 3 µM fluo-3 was added. Fluo-3 fluorescence was monitored at 490 nm excitation and 535 nm emission in a 250-µL cuvette, held at 17° C. with a circulating water bath and continuously mixed with a magnetic stirring bar, in a Hitachi spectrofluorometer (F-2000).

Detection of NAD by Cycling Assay

Mouse tissues were frozen in liquid $N_2$, pulverized into a powder, and extracted with 10% trichloroacetic acid (TCA) at 4° C. TCA was removed with water-saturated ether. The aqueous layer containing the NAD was removed and adjusted to pH 8 with 1 M Tris. Detection of NAD was determined as described elsewhere (Aksoy et al., *Bichem. Biophys. Res. Commun.,* 345:1386-1392 (2006); and Aksoy et al., *Biochem. Biophys. Res. Commun.,* 349:353-359 (2006)).

PGC-1α analysis

PGC-1α analysis was performed by direct western-blot analysis using a rabbit anti-PGC-1α antibody (H-300, Santa Cruz Biotechnology, Santa Cruz, Calif.).

Fecal Analysis

Daily fecal outputs were determined on metabolic cages and measured by collecting all feces from each individual mouse (3-4 mice/day) for 7 days. Feces were allowed to air dry at least 72 hours before weighing. Total lipids were extracted by the Folch method (Folch et al., *J. Biol. Chem.,* 226:497-509 (1957)).

Histological Analysis

Histological analyses, including hematoxylin/eosin staining (HE) and electron microscopy (EM), were performed using standard techniques as described elsewhere (Baur et al., *Nature,* 444:337-342 (2006)). Mitochondria in EM images were quantified using Image J version 1.36b. Histological specimens were analyzed by three different pathologists that classified the liver tissue as normal, mild, moderate, or severe steatotic. All three independent clinical pathologists agree with the diagnosis of moderate steatosis in liver samples from wild type mice fed a high fat diet.

Biochemical Markers, Hormones, and Fatty Acids

Plasma levels of non-esterified fatty acids were measured using the NEFA C kit (Wako Chemicals, Richmond, Va.) according to the manufacturer's instructions. Leptin was measured using an ELISA kit (R&D Systems, Minneapolis, Minn.).

Oxygen Consumption, Carbon Dioxide Production, and Activity

Each mouse was acclimated to a 30 cm×10 cm cylindrical chamber for 24 hours prior to the measurement of 24-hour energy expenditure (EE) using a small animal calorimeter. Physical activity was measured using Opto-M Varimex Minor activity monitor that uses infrared beam breaks in three axes to measure activity (Columbus Instruments; Novak et al., *J. Neuroendocrinol.,* 18:594-601 (2006)). Physical activity data were collected each minute in three axes using infrared beam break counts (ambulatory=non-repetitive horizontal beam breaks; total counts=horizontal+ambulatory+vertical counts; stationary counts=ambulatory-horizontal). The calorimeter was set to deliver room air 0.60-0.65 L/minute to the chamber and collect samples every minute (with a 5 minute reference period every 30 samples) with a sample flow of 0.4 L/minute. Resting energy expenditure (REE) was calculated by averaging the energy expenditure (EE) values associated with 0 activity counts for the minute of the EE measurement and the four prior minutes. Activity EE (EEA) was calculated by subtracting REE from total energy expenditure (TEE).

Oxygen consumption and carbon dioxide production were measured by using a customized, high-precision, single-chamber indirect calorimeter (Columbus Instruments, Columbus, Ohio, USA) as described elsewhere (Thompson et al., *Am. J. Physiol. Endocrinol. Metab.,* 287:E1142-1148 (2004)). Thermogenesis was calculated from oxygen consumption and carbon dioxide production. Calibration of the calorimeter was performed at the beginning of each measurement day. The animal was placed inside the cylindrical calorimeter chamber (acrylic; diameter 30 cm, height 20 cm, volume 15 L). The chamber lid was attached and sealed, and room air was pumped at atmospheric pressure through the chamber at 3.4-3.7 L/minute. Data on oxygen consumption and carbon dioxide production were then collected every minute and stored on a PC. Each data-point was identified by a time-stamp. Ambulation was measured simultaneously with the oxygen consumption and carbon dioxide production measurements. Measurements were performed using customized, high-precision racks of collimated infrared activity sensors (Columbus Instruments) placed around the acrylic chamber. There were 45 collimated beams of infrared light crossing the 30-cm-diameter cage, allowing the detection of 1 inch of movement in three orthogonal axes. Photosensors registered an activity unit each time a beam was interrupted. In this fashion, activity was simultaneously detected in all three axes: forward-and-backward, side-to-side, and up-and-down. Data for ambulation were summed for every minute and stored on the PC with use of the time stamp for identification. Data were thereby derived simultaneously for oxygen consumption and ambulation, for each animal, every minute over the 24 hour measurement period. Animals were acclimated for 24-48 hours before the measurements.

Materials

All other reagents were supplied from Sigma Chemical (St. Louis, Mo.). *L. pictus* and *Aplysia californica* were obtained from Marinus Inc. (Long Beach, Calif.). Fluo-3 was purchased from Molecular Probes (Eugene, Oreg.). cADPR were synthesized as described elsewhere (Macleod et al., *Genes Dev.,* 9:935-44 (1995)).

Statistical Analysis

Data were presented as mean s.e.m. The main and interactive effects were analyzed by analysis of variance (ANOVA) factorial, repeated measurements or by one-way ANOVA. Differences between individual group's means were analyzed by Fisher's test. Analyses were performed using sigma plot statistics.

Results

CD38 is a Regulator of SIRT-PCG1α Pathway

Figure 2:
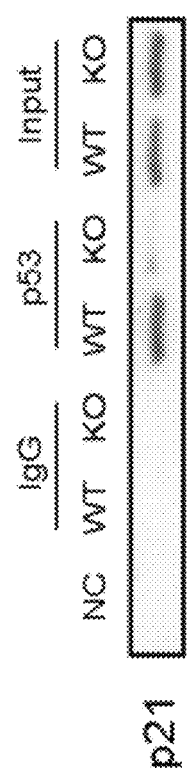
FIG. 2. P53 and P21 function in wild type and CD38 (−/−) mice. In A, Chromatin fragments from wild type and CD38 null mice cells were immunoprecipitated with anti-p53 antibody. Immunoprecipitated chromatin was analyzed by PCR to determine p53 occupancy of the p21 promoter. PCR analysis on input chromatin (last two lanes) confirmed that equal chromatin amounts were used for ChIP. NC represents a PCR negative control. In B, P21 promoter luciferase assays were performed in vitro using smooth muscle cells from wild type and CD38 (−/−) mice. All experiments were repeated at least 3-4 times.
Figure 2:
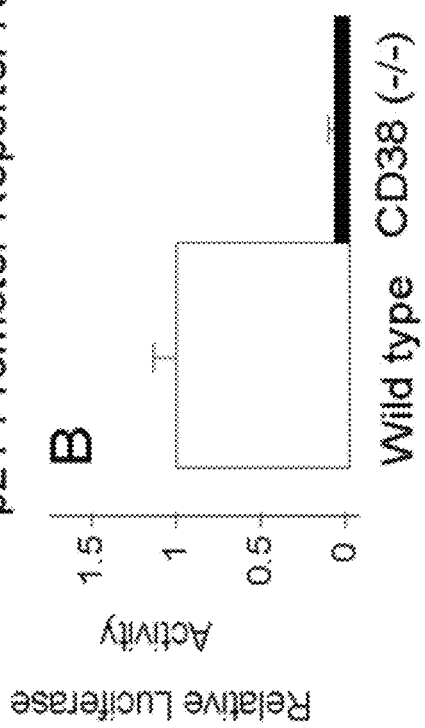

CD38 (−/−) mice exhibited increased levels of NAD and sirtuin activity, without exhibiting changes in SIRT1 levels, in tissues that play a role in the regulation of body weight including liver, muscle, brain, and heart (FIGS. 1A-C). Using acetylation status and transcriptional activity of the SIRT target p53 as a surrogate marker of endogenous sirtuin activity, in vivo sirtuin activity was shown to increase not only in muscle (FIG. 1A), but also in liver (FIG. 1B), brain (FIG. 1D), and heart. Using a combination of expression, chromatin immunoprecipitation, and reporter assays, levels of acetylated p53 were found to decrease in cells from CD38 (−/−) mice (FIG. 1E). Acetylated p53 functional activity was impaired in cells from CD38 (−/−) mice as demonstrated by decreased binding to the promoter of one its target genes, p21. Furthermore, cells from CD38 (−/−) mice exhibited decreased p53-mediated p21 promoter activity (FIG. 2). Treatment with resveratrol can lead to SIRT activation (Baur et al., *Nature*, 444:337-342 (2006) and Lagouge et al., *Cell*, 127:1109-1122 (2006)), that in turn, can deacetylate PGC1α and can increase its intracellular levels (Baur et al., *Nature*, 444:337-342 (2006); Lagouge et al., *Cell*, 127:1109-1122 (2006); and Rodgers et al., *Nature*, 434:113-118 (2005)). Consistent with the SIRT activation, levels of PGC1α were increased several fold in liver from CD38 (−/−) mice (FIG. 1F).

Protective Effect of CD38 Deficiency Against High Fat Diet-Induce Obesity

To determine the role of CD38 upon high fat diet-induced obesity, fully developed middle age mice were evaluated. As animals reach adulthood, their growth rate decreases and fat is stored as an energy reserve in adipose tissue, thus leading to obesity. Wild type and CD38 (−/−) mice were followed for over one year. Adult wild type and CD38 (−/−) mice maintained on standard chow diet (4% total calories derived from fat, 3.04 kcal g-1) differ slightly on weight. The CD38 (−/−) mice were consistently thinner by about 3 g (Table 1). Furthermore, the abdominal and inguinal adipose tissues were also reduced in CD38 (−/−) mice (Table 1). This decrease in fat accumulation in CD38 (−/−) mice was not due to less food intake or malabsorption (Table 1) since food intake, fecal output, and fat content were not significantly different between both mice genotypes (Table 1). Analysis of other biochemical parameters including insulin, leptin, adiponectin, glucose, ketone body formation, and free fatty acids levels did not reveal any differences between the wild type and CD38 (−/−) mice.

Figure 3:
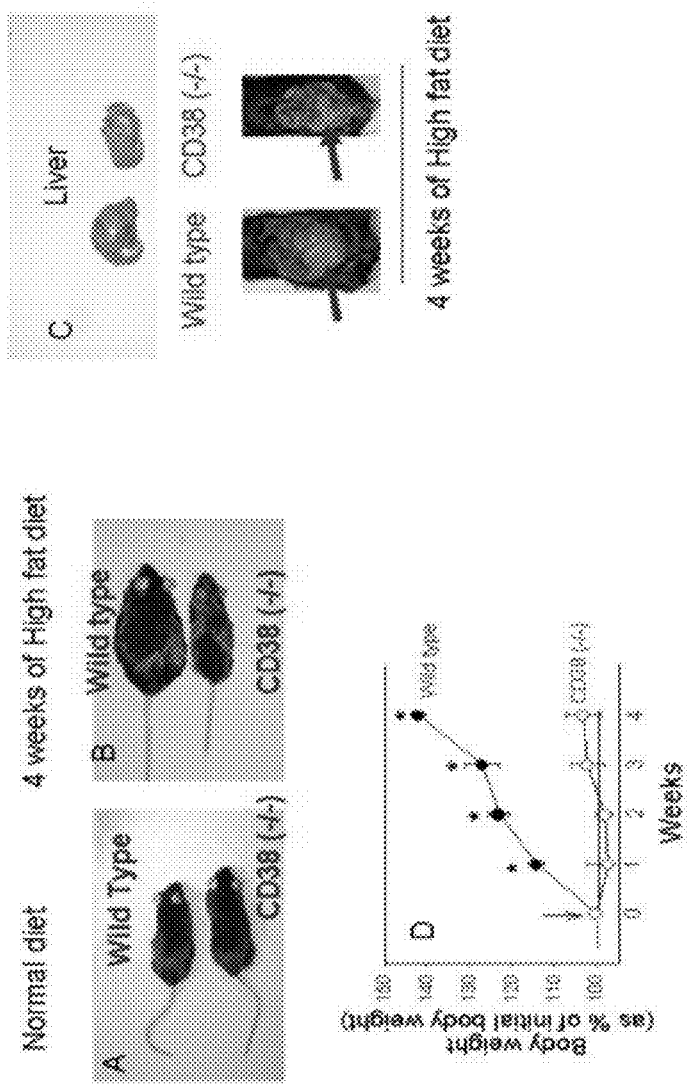
FIG. 3. CD38 knock out mice are protected against high fat diet-induced obesity. In A and B, representative pictures of wild type and CD38 (−/−) mice were taken before and after 4 weeks of high fat diet (HFD). The wild type mice in the picture gain about 45% of its body weight after 4 weeks of HFD. The CD38 (−/−) gained no weight during the study. In C, a picture of representative livers and abdominal fat pad in wild type and CD38 (−/−) mice was taken after 4 weeks of HFD. Panel D is a graph of the weekly weight gain in wild type and CD38 (−/−) mice fed an HFD. The symbol (*) denotes significantly difference between wild type and CD38 (−/−). Follow up of the animals for 2 weeks before the beginning of the HFD revealed no increase in body weight on normal chow diet. The arrow indicates the initiation of the HFD.
Figure 4:
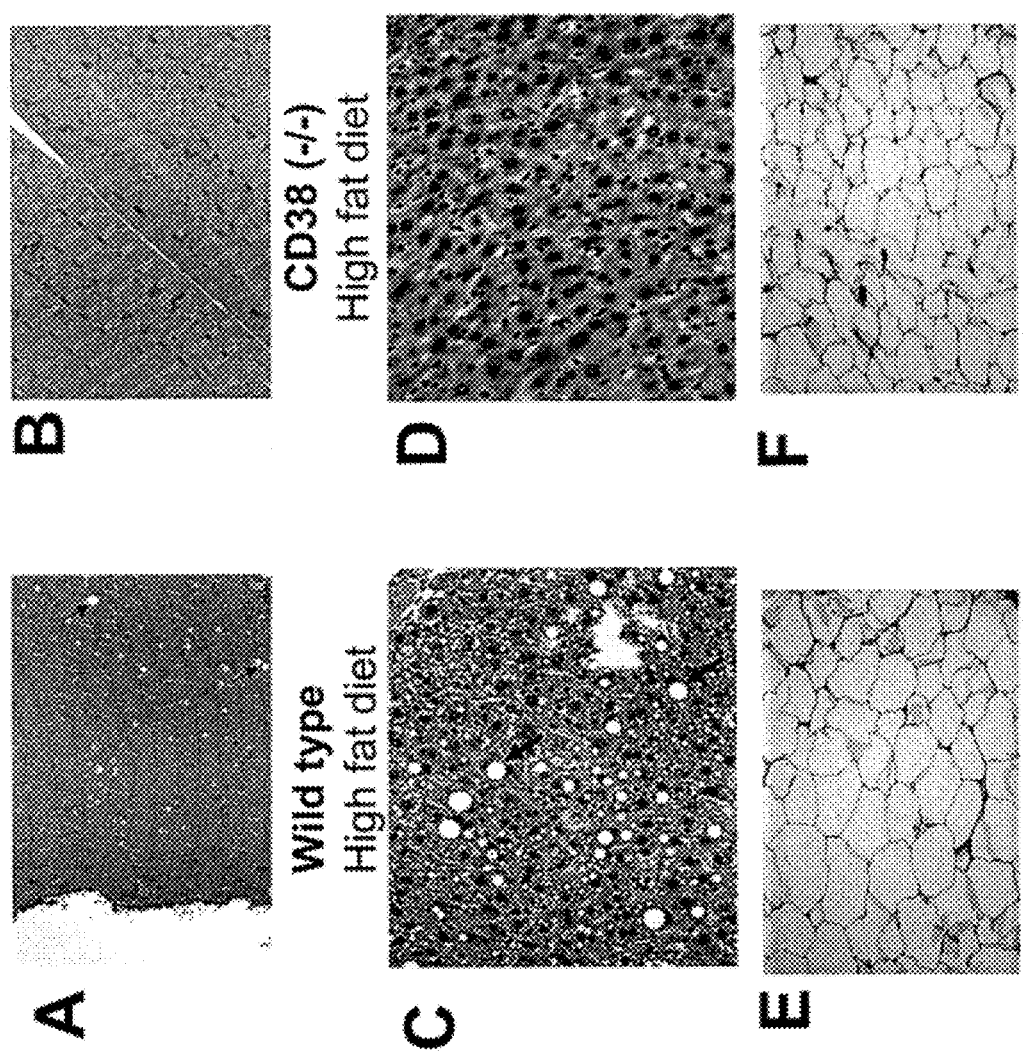
FIG. 4. Microscopic analysis of fat infiltration in wild type and CD38 knock out mice fed HFD. In A trough F, representative pictures were taken of skeletal muscle, liver and fat tissues from wild type (A, C, E) and CD38 (−/−) (B, D, F) mice after 4 weeks of HFD (except for the liver samples that were obtain after 6 weeks of HFD). The wild type mice in the picture gained about 45% of its body weight after 4 weeks of HFD. The CD38 (−/−) mice gained no weight during the study. In A and B, the electron microscopy of skeletal reveals fat droplets (arrows) in wild type but not CD38 (−/−) mice. In C, moderate liver steatosis was observed in wild type mice using H&E stains after 6 weeks of HFD. In D, no steatosis was observed in CD38 (−/−) mice after 6 weeks of HFD. In E and F, a comparison of adipocytes from wild type and CD38 (−/−) mice reveals that cells from wild type mice were larger and had a greater accumulation of fat. All slides were analyzed by three independent clinical pathologists. All three pathologists agree with their diagnosis of increase fat infiltration in skeletal muscle, liver and adipocytes of wild type mice.

To further evaluate the role of CD38 on obesity, mice were challenged with high caloric-fat diet (60% of calories from fat, 5.05 kcal g-1). When CD38 (−/−) mice were fed with a high fat diet, weight accumulation was nearly absent when compared with wild-type mice during the feeding period (FIG. 3). To determine the amount of weight gain corresponding to fat, mice were sacrifice at four weeks of high fat diet, and the total abdominal and inguinal fat were dissected (Table 1, FIGS. 3 and 4). Assessment of total abdominal and inguinal fat pads revealed that the body fat in CD38 (−/−) mice did not increase over this period, whereas it nearly quadruple for wild-type mice (Table 1). In addition, microscopic evaluation of adipocytes in cells from wild type and CD38 (−/−) mice indicate a larger accumulation of fat in cells from wild type mice. Liver size increased in wild type mice due to fat infiltration, but liver size was not altered in CD38 (−/−) mice (Table 1, FIGS. 3 and 4). Wild type mice placed on high fat diet for six weeks exhibited moderate liver steatosis (FIG. 4). In addition, fat accumulation in other organs like skeletal muscle was also prevented by knocking out CD38 expression (FIG. 4).

Figure 5:
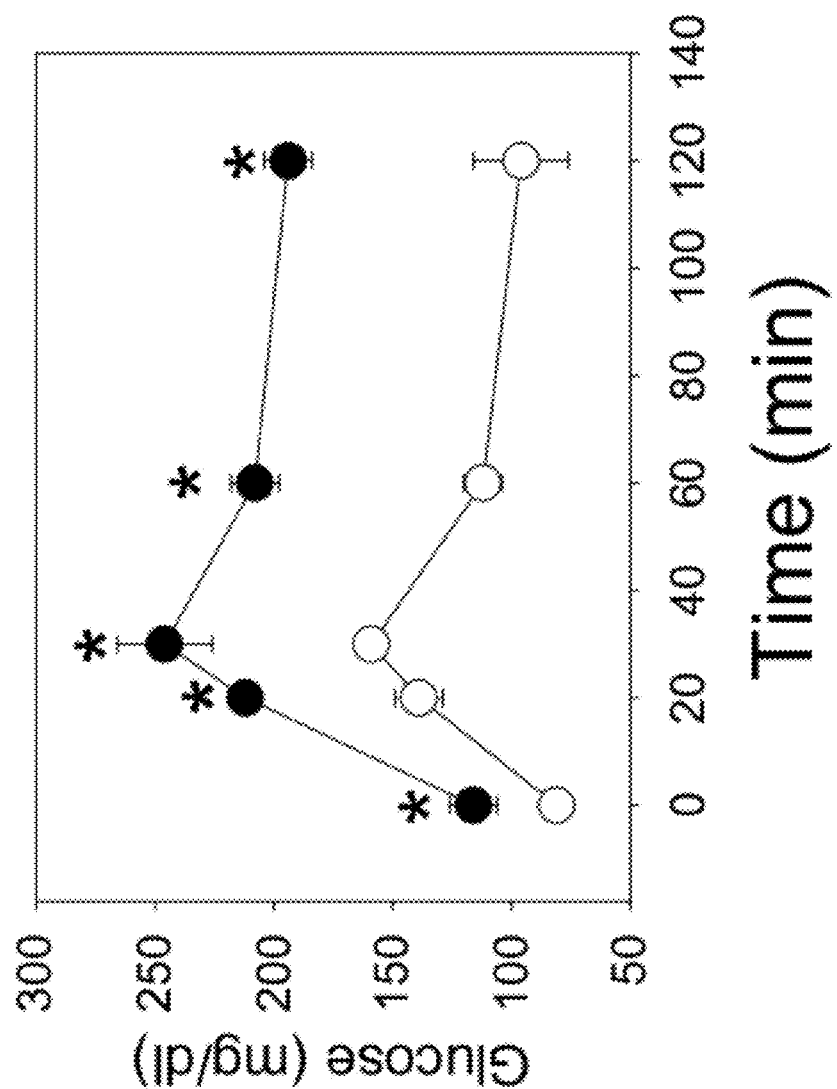
FIG. 5. Gluocose tolerance test in wild type (filled circles) and CD38 knock out (open circles) mice on HFD. Time course of plasma levels of glucose were measured after 1.5 g/Kg intraperitoneal injection of a 20% glucose solution. Mice were fed HFD for 8 weeks, and the night before the test were starved for 12 hours. Samples were obtained from the tail vein, and glucose analyzed using a glucose oxidase based kit. All measurements were repeated at least three times. The asterisk denotes significant difference $p<0.05$.

Protective Effect of CD38 Knock Out Against High Fat Diet Induced Glucose Intolerance A metabolic consequences of obesity is the development of diabetes and glucose intolerance (Puigserver, *Intl. J. Obesity*, 29:S5-S9 (2005); Baur et al., *Nature*, 444:337-342 (2006); and Lagouge et al., *Cell*, 127:1109-1122 (2006)). The role of CD38 on the development of glucose intolerance induced by high fat diet was examined (FIG. 5). Wild type and CD38 (−/−) mice fed a standard chow diet did not exhibit different glucose tolerance. After 8 weeks of high fat diet, however, wild type mice became glucose intolerant. In contrast, no significant changes were observed on glucose tolerance tests in CD38 (−/−) mice (FIG. 5). These results demonstrate that CD38 is not required for insulin secretion and maintenance of

TABLE 1

Biochemical and physiological parameters of wild type and CD38 (−/−) mice on standard diet and HFD.

| Parameter | Standard Diet | | HFD | | |
|---|---|---|---|---|---|
| | Wild type | CD38 (−/−) | Wild type | CD38 (−/−) | |
| Free fatty acids (mequiv.) | 0.14 (0.02) | 0.11. (0.02) | 0.4 (0.02)# | 0.3 (0.01)# | |
| Insulin (ng ml$^{-1}$) | 0.18 (0.03) | 0.14 (0.02) | 6.2 (0.8)# | 4.3 (0.34)# | |
| Glucose (mg dl$^{-1}$) | 134.0 (6) | 128 (8) | 120.3 (5) | 110 (4) | Fed |
| Glucose | 92. (9) | 98 (4) | | | Fasted |
| Leptin (ng ml$^{-1}$) | 1.4 (0.1) | 1.5 (0.1) | 19 (3)# | 6 (0.3)#* | |
| Food intake (g/day) | 2.8 (0.8) | 3.2 (0.7) | 2.7 (1) | 3.3 (1.2) | |
| Food intake (kcal /day) | 8.5 (2.4) | 9.7 (2.0) | 13.6 (5)# | 16.7 (5.5)#* | |
| Weight at end of study (g) | 30 (2) | 27 (2) | 45.2 (2)# | 26 (2)* | |
| Abdominal fat (g) | 1.9 (0.3) | 1.2 (0.4)# | 7.3 (1.2)# | 1.35 (0.8)* | |
| Liver weight (g) | 1.2 (0.3) | 1.3 (0.5) | 1.8 (0.2)# | 1.35 (0.3) | |
| Body temperature (° C.) | 34.3 (0.1) | 34.5 (0.1) | 35.5 (0.2) | 35.6 (0.2) | |
| Fecal fat (mg/g) | 7 (1) | 6 (2) | 28 (5)# | 25 (5)# | |
| β-Hydroxybutirate (mg dl$^{-1}$) | 1.0 (0.02) | 1.2 (0.03) | ND | ND | Fasted |

All measurements were repeated at least 3-4 times. End of the study was 4 weeks of HFD.
ND denotes not determined.
Values shown are mean (± s.e.m.).
The following signs indicate statistical significance.
*= P < 0.05 versus wild type high fat diet.
= P < 0.05 versus standard diet.
Levels of thyroid hormones did not differ between wild type and CD38 (−/−) mice.

normal glucose metabolism. These results also demonstrate a beneficial effect of reducing CD38 expression in glucose metabolism in vivo.

Enhanced Energy Expenditure in CD38 Null Mice

Figure 6:
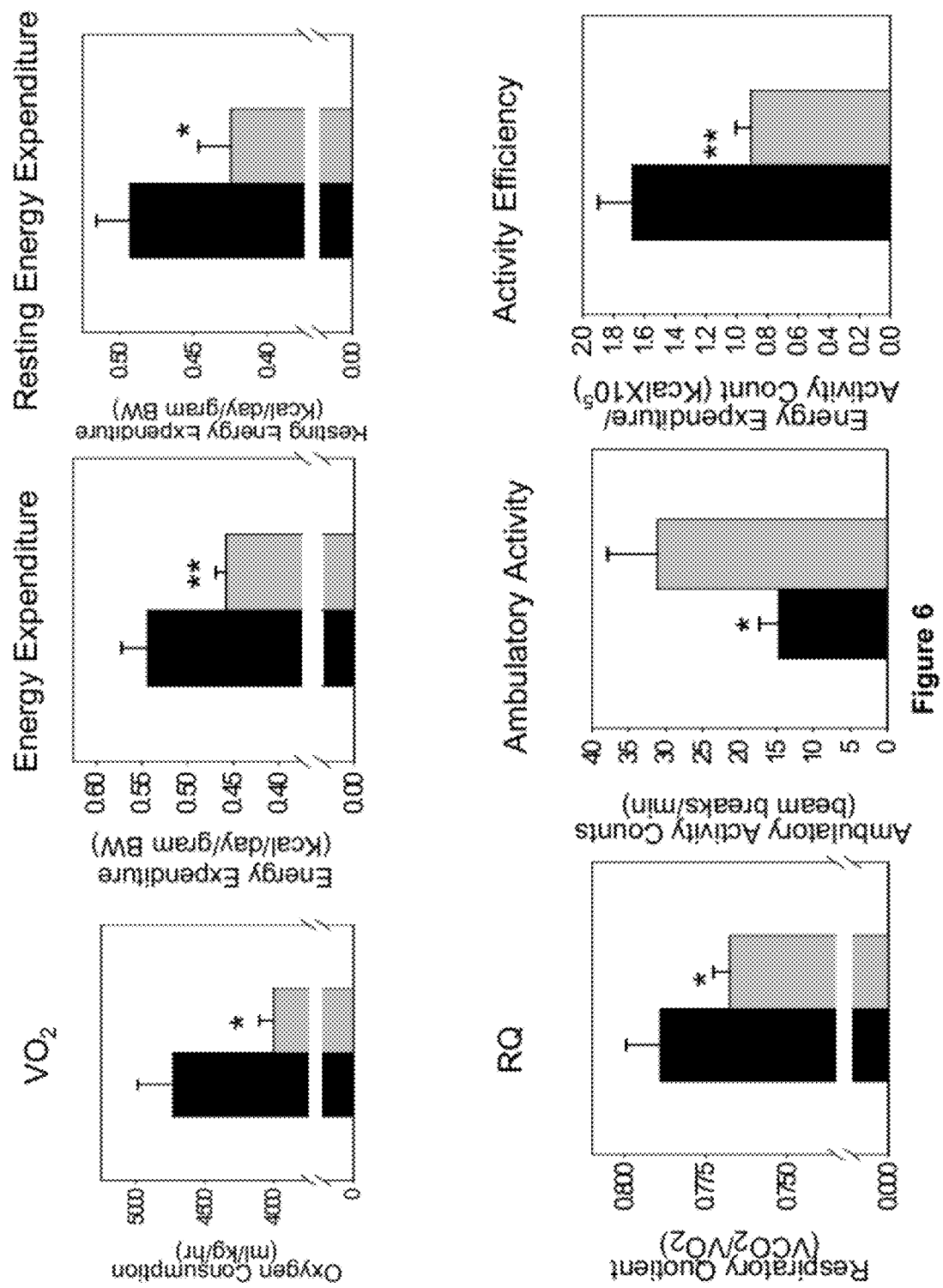
FIG. 6. Energy expenditure and activity in CD38 (−/−) and wild type mice feed HFD for two weeks. Oxygen consumption (mL/kg/hour), energy expenditure (Kcal/day/g BW), and resting energy expenditure (kcal/day/g BW) were all greater in CD38 (−/−) mice (black bars) compared to wild types mice (gray bars), as was respiratory quotient (RQ: $VCO_2/VO_2$). Wild type mice exhibited significantly more ambulatory activity counts than CD38 (−/−) mice, but the energy efficiency of activity [$10^{-5}$×Kcal energy expended for every (horizontal+vertical) activity count)] was higher in the CD38 (−/−) mice. *$p<0.05$, **$p<0.01$. Measurements were performed on six mice from each group.

Although food intake in CD38 (−/−) mice was similar to that of wild-type mice, when normalized to body weight they consumed 40% more food (Table 1). Moreover, on the basis of similar fecal output and fecal fat content, the protection against weight gain of the CD38 (−/−) mice was not due to malabsorption of fat (Table 1). Therefore, these results indicate that the CD38 (−/−) mice can have higher energy expenditure than wild type mice. Thus, the energy homeostasis in CD38 (−/−) and wild type mice fed a high fat diet was investigated. Using a high precision indirect calorimeter, the CD38 (−/−) mice were found to have significantly higher oxygen consumption ($VO_2$) and energy expenditure (EE) corrected for body weight compared to the wild type mice (Table 2). Resting energy expenditure (REE) corrected for body weight was also significantly greater in the CD38 knockout mice (FIG. 6). The wild type mice exhibited greater amounts of physical activity (horizontal, vertical, ambulatory, and total activity counts) compared to the CD38 knockout mice (FIG. 6 and Table 2).

metabolism and mitochondrial biogenesis. Since in CD38 (−/−) mice both basal and activity-related metabolic rates were increased, it is possible that more than one tissue is involved on changes in energy expenditure.

Figure 7:
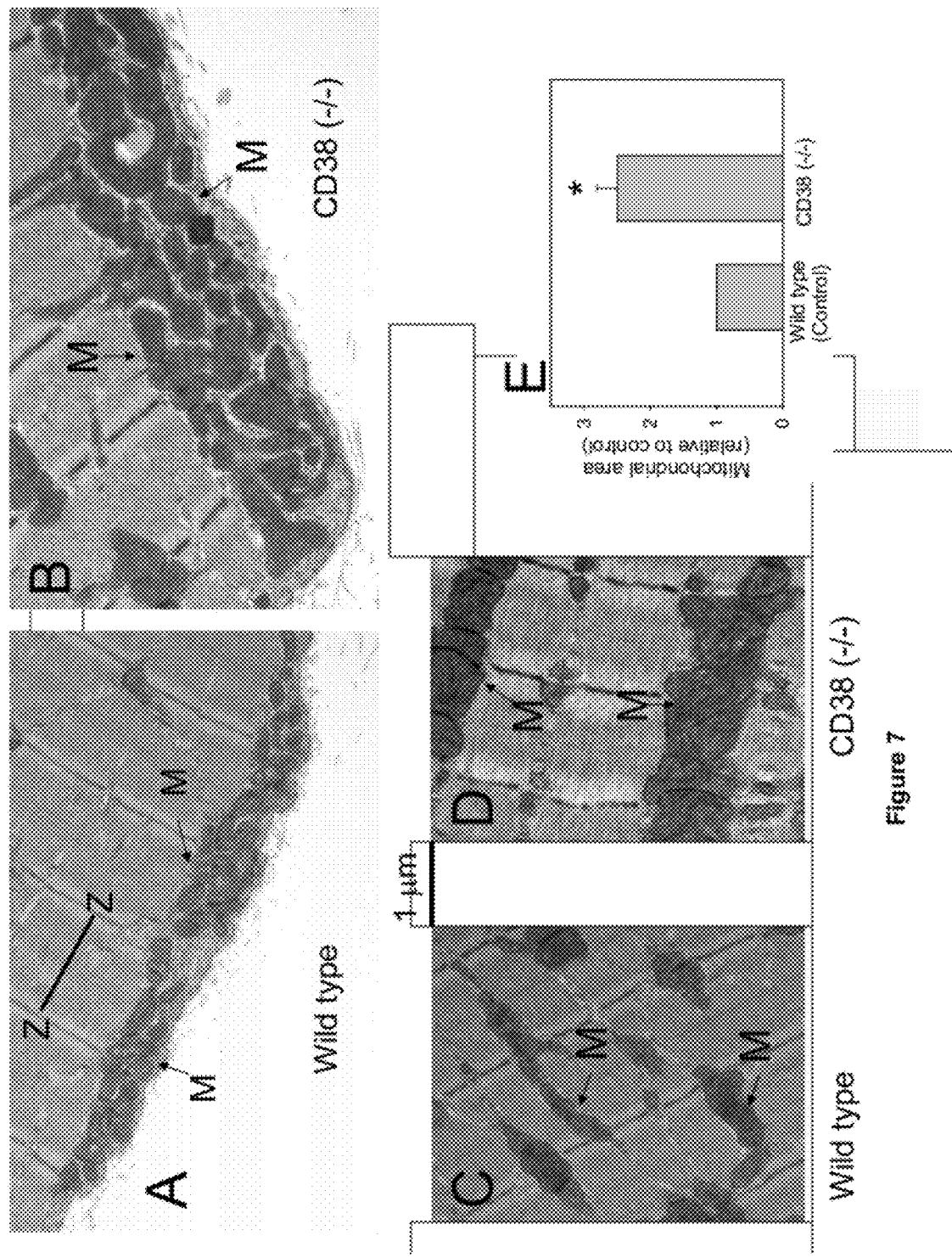
FIG. 7. Increased mitochondrial area in CD38 knock out mice. Muscle biopsies were obtained from gastrocnemicus muscle (red muscle) from wild type (A and C) and CD38 (−/−) (B and D) one year old mice, and their mitochondrial morphology was analyzed by electron microscopy in both subsarcolemal (A and B) and intersarcomeric (C and D) regions. In both regions, CD38 (−/−) mice exhibited larger mitochondrial area then wild type mice, which represented an increase of about 2.5 times as determined by total mitochondrial area determination in five different regions of the muscle (E). Mitochondrial morphology and number did not differ significantly in liver cells from the same animals. All experiments were repeated at least three to four times. The asterisk denotes significant difference $p<0.05$.

The morphological changes in mitochondria in skeletal muscle were investigated. As shown in FIGS. 4 and 7, the size and number of the mitochondria in gastrocnemicus muscle from CD38 (−/−) mice were increased compare to those of wild type mice. The calculated mitochondrial area was increased 2.5 times in CD38 (−/−) mice (FIG. 7), which is compatible with a role of skeletal muscle on the increase in energy expenditure in C38 (−/−) mice. These results further demonstrate that the effect of CD38 on obesity and energy expenditure is mediated by the SIRT1-PGC1α pathway.

CD38 Deficiency Protective Effect on High Fat Diet-Induced Obesity Requires an Intact SIRT Activity CD38 has been implicated as an enzyme responsible for the synthesis of the second messenger cyclic-ADP-ribose (Galione and Churchill, *Sci. STKE.*, 41:PE1 (2000)). To further determine if the regulation of SIRT by CD38 was mediated by cADPR-induced $Ca^{2+}$ release or modulation of the activity of SIRT, the effect of pharmacological agonists and antagonists of the SIRT system upon cADPR synthesis and

TABLE 2

Calorimetric and activity measurements in wild type and CD38 (−/−) mice after 2 weeks of high fat diet.

| | $VO_2$ (mL/kg/hr) | RQ | TEE (Kcal/day) | TEE/BW (Kcal/day/g) | REE (Kcal/day) | REE/BW (Kcal/day/g) | EEA (Kcal/day) | Activity Efficiency (Kcal/count) × $10^{-5}$ |
|---|---|---|---|---|---|---|---|---|
| CD38 (−/−) | 4731 ± 255 | 0.789 ± 0.011 | 13.03 ± 0.321 | 0.544 ± 0.028 | 11.815 ± 0.116 | 0.493 ± 0.023 | 1.254 ± 0.235 | 1.680 ± 0.220 |
| WT | 4003 ± 101 | 0.76 ± 0.005 | 16.318 ± 0.297 | 0.458 ± 011 | 15.109 ± 0.300 | 0.424 ± 0.013 | 1.209 ± 0.330 | 1.908 ± 0.097 |
| p-value | <0.05 | <0.05 | <0.0001 | <0.01 | <0.00001 | <0.05 | =0.46 | <0.01 |

| | Activity Counts | | | | |
|---|---|---|---|---|---|
| | Horizontal | Ambulatory | Vertical | Total | Stationary |
| CD38 (−/−) | 47 ± 5.6 | 15 ± 2.6 | 5.6 ± 1.4 | 68 ± 8.9 | 32 ± 4.1 |
| WT | 69 ± 10.2 | 31 ± 6.7 | 16.7 ± 4.8 | 117 ± 21.4 | 38 ± 3.5 |
| p-value | <0.05 | <0.05 | <0.05 | <0.05 | =0.16 |

RQ = respiratory quotient, $VCO_2/VO_2$
TEE = total energy expenditure
BW = body weight (in g)
REE = resting energy expenditure
EEA = energy expenditure of activity
Activity Efficiency = [(EEA/min)/([counts(horizontal + vertical)]/min)] × $10^{-5}$ Respiratory quotient (RQ) was significantly higher in the CD38 (−/−) mice as compared to the levels in wild type mice. Energy expenditure of activity (EEA) was similar between the groups of mice, but EEA per activity count (horizontal+vertical) was significantly higher in the CD38 (−/−) mice (almost twice the value of that observed for wild type mice), suggesting that the calculated efficiency of movement was lower in the CD38 knockout mice (FIG. 6). These changes can contribute to the ability of these mice to fend off weight gain during high fat diet-feeding, even with decreased ambulation. Taken together, these results demonstrate that the CD38 deficiency protective effect against high fat diet-induced obesity can be mediated by enhanced energy expenditure.

Figure 8:
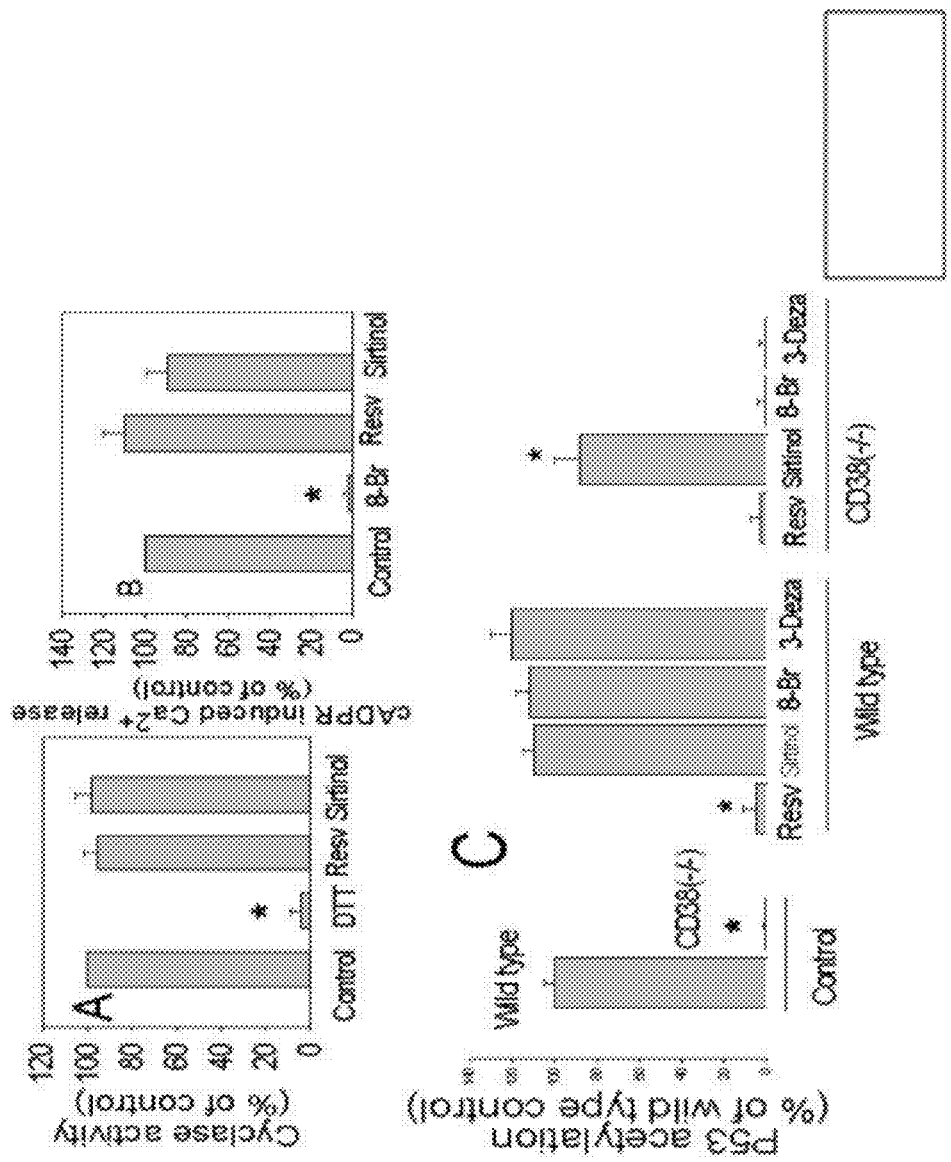
FIG. 8. The effect of resveratrol and sirtinol upon the cADPR system. In A, ADP ribosyl cyclase activity was measured in liver plasma membranes using NGD as a substrate. Mice were treated with 100 μM of a test drug: DTT (dithiothreitol), resverastrol (Resv), or sirtinol. The control mice received no addition. Similar results were obtained using purified Aplysia ADPribosyl cyclase. In B, cADPR-induced $Ca^{2+}$ was measured in sea urchin egg homogenates. $Ca^{2+}$ was induced by 100 nM of cADPR with no further additions, or with 1 minute pre-incubation of 100 μM of the testing drugs 8-Br-cADPR (8-Br), resveratrol (Resv), or sirtinol. In C, experiments were conducted in smooth muscle cells in culture as described in FIG. 1E. Four to six hours before fixation and staining with acetylated P53 antibody, cells were treated with 100 μM of the testing drugs. 3-Deaza-cADPR is a cell permeable cADPR agonist. In control experiments using the same conditions, incubation with 8-Br-cADPR blocked $Ca^{2+}$ release induced by oxytocin, and 3-Deaza-cADPR increased oxytocin effect. These results indicate that the cADPR agonist and antagonist are effective in smooth muscle cells. All experiments were repeated three to four times. The asterisk denotes significant differences between control and treatment.

While not being limited to any particular mode of action, the mechanism that underlines the increase in energy expenditure in CD38 (−/−) mice can be mediated by augmented PGC1α activity and its downstream effects upon energy cADPR-induced $Ca^{2+}$ release was determined (FIG. 8). Neither resveratrol (a SIRT activator) nor sirtinol (a SIRT inhibitor) exhibited any effect upon these parameters. Moreover, the effect of SIRT and cADPR pharmacologic modulators upon in vivo acetylation of p53 as a measure of endogenous SIRT activity was investigated. Sirtinol increased acetylated p53 in cells from CD38 (−/−) mice, and resveratrol decreased acetylated p53 in cells from wild type mice (FIG. 8). In contrast, neither the cell permeable cADPR antagonist (8-br-cADPR) nor the cADPR agonist (3-deaza-cADPR) had any effect upon the levels of p53 acetylation in cells (FIG. 8).

Figure 9:
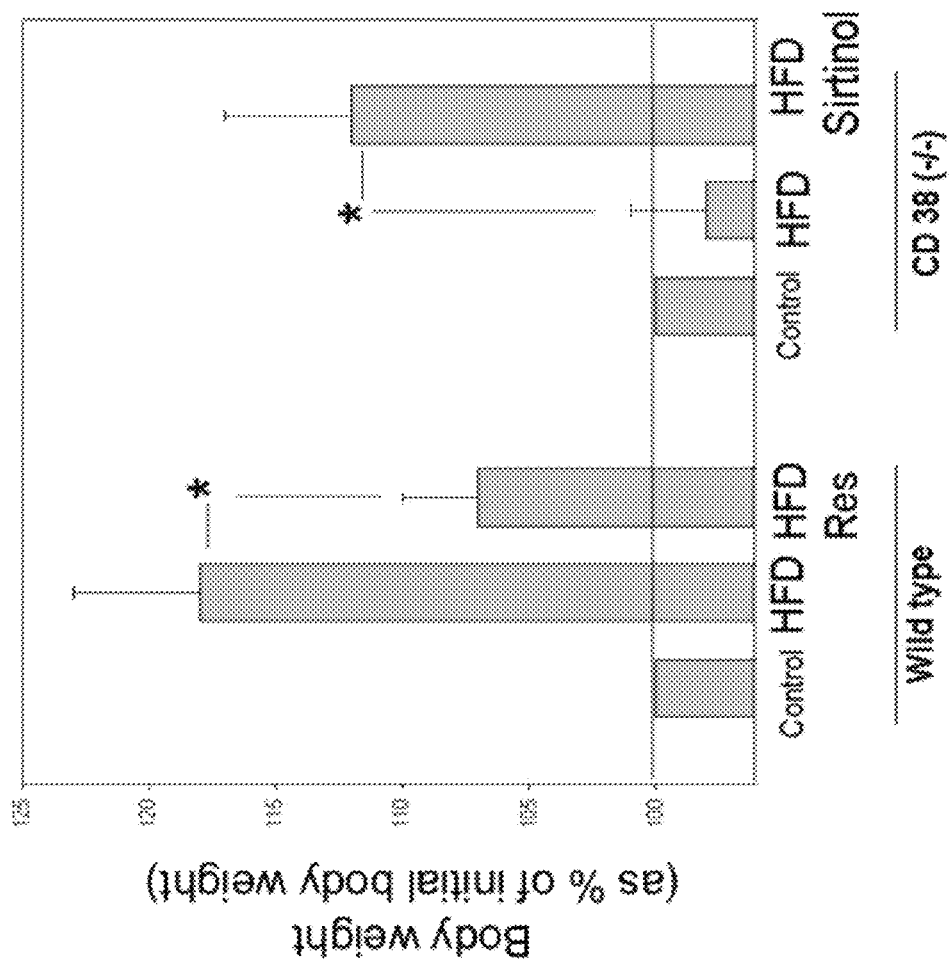
FIG. 9. Sirtinol, a SIRT inhibitor, prevents the protective effect of CD38 deficiency against high fat diet-induced obesity. Wild type mice were treated with resveratrol (a SIRT stimulator), and CD38 (−/−) mice were treated with Sirtinol (a SIRT antagonist) during 2 weeks of high fat diet. Resveratrol provided protection of the wild type against HFD-induced obesity. On the other hand, sirtinol abrogates the weight gain resistance of the CD38 (−/−) mice. The asterisk indicates significant differences. Neither food intake nor fecal output were significantly different between groups. The number of animals in each group was between four and six.

Wild type mice were treated with 30 mg/kg/day of resveratrol, and CD38 (−/−) were treated with the same dose of sirtinol to determine the role of the SIRT enzymes upon high fat diet-induced obesity. Wild type mice treated with resveratrol for two weeks were protected against high fat induced obesity (FIG. 9). In contrast, the protective effect of the CD38 knock out upon high fat diet-induced obesity was abrogated by sirtinol. Sirtinol treated CD38 (−/−) mice gained a statistically significant amount of weight when compared with non-sirtinol (vehicle) treated CD38 (−/−) mice (FIG. 9). These results demonstrate that CD38 can modulate high fat diet-induced obesity by a sirtuin dependent mechanism.

In summary, the results provided herein demonstrate that CD38, via regulation of NAD levels, can control SIRT activity and activation of PGC1α, which in turn, can regulate energy metabolism and obesity.

Longevity

Figure 10:
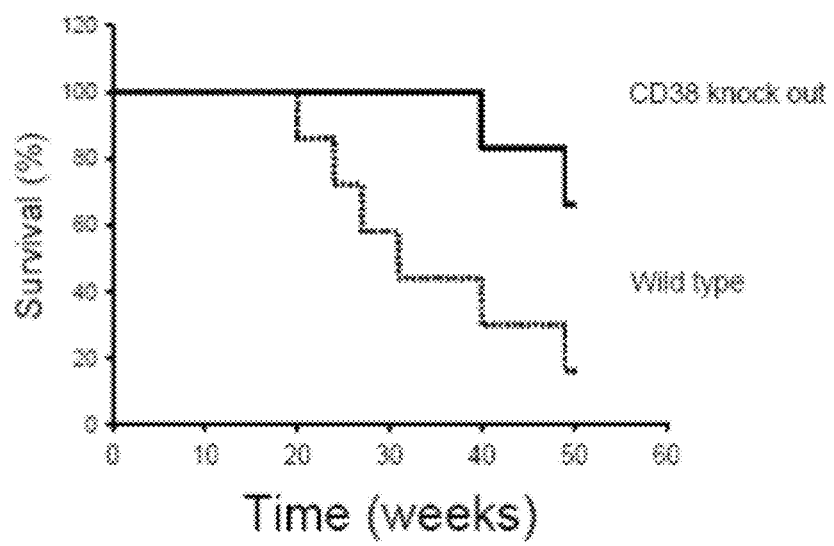
FIG. 10. Increase longevity of CD38 knock out mice on high fat diet. One year old wild type and CD38 (−/−) mice were treated with high fat diet for about 50 weeks, and their natural mortality was determined. At the end of 35 weeks, none of the CD38 (−/−) had died, and about 55% of the wild type mice were dead.

One year old wild type and CD38 (−/−) mice were treated with high fat diet for about 50 weeks, and their natural mortality was determined. At the end of 35 weeks, none of the CD38 (−/−) had died, and about 55% of the wild type mice were dead (FIG. 10).

CD38 Appears to be a the Main NADase in Tissues

Figure 11:
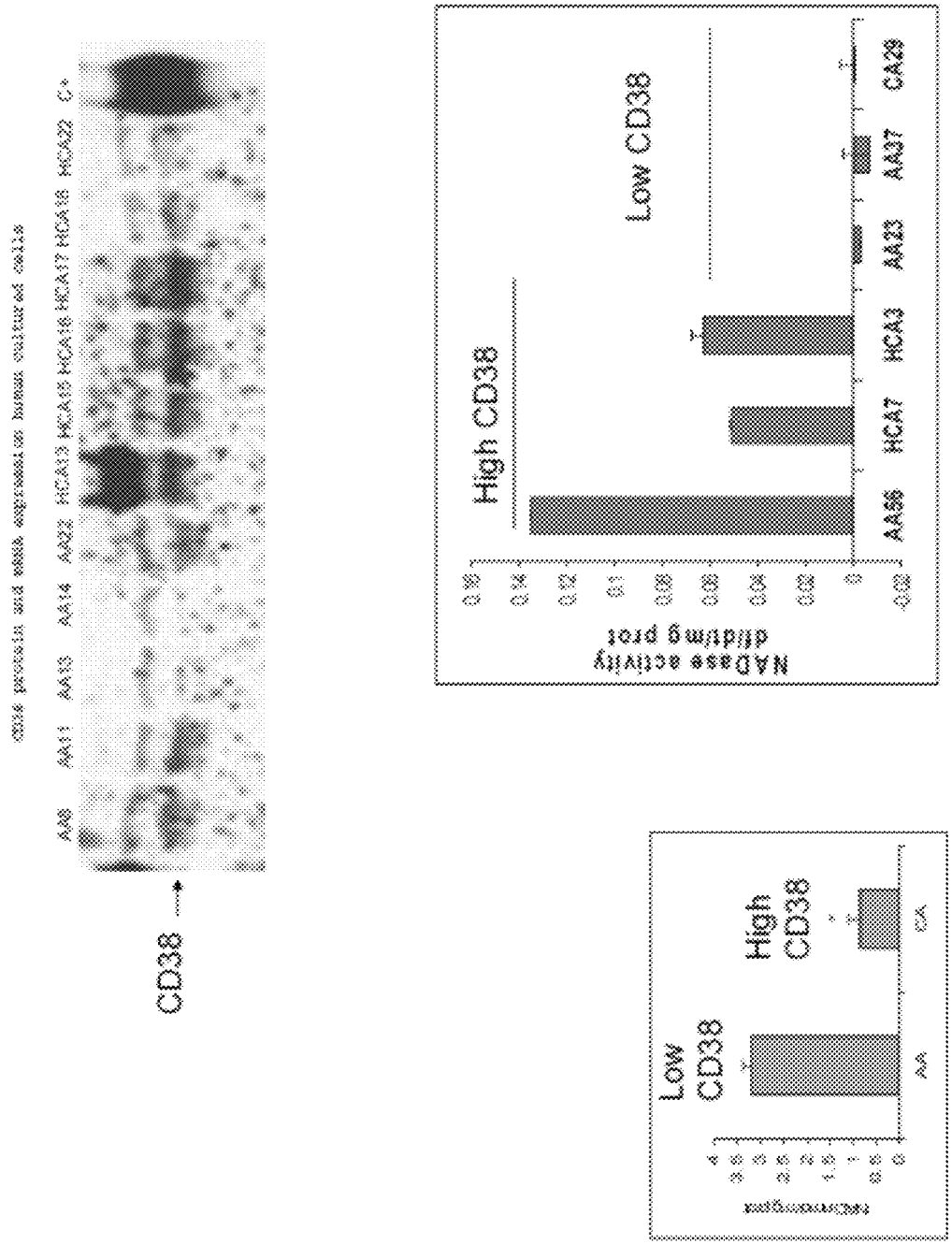
FIG. 11. Correlation between CD38 mRNA, CD38 polypeptide, NADase, and NAD levels in human cultured cells. Cells from a genomic database were screen for mRNA, polypeptide, and CD38 NADase activity. A correlation was observed between mRNA, polypeptide, and NADase expression. Furthermore, cells with high CD38 expression exhibited lower NAD levels and higher nicotinamide levels. In contrast, cells with low CD38 expression exhibited higher NAD and lower nicotinamide.
Figure 11:
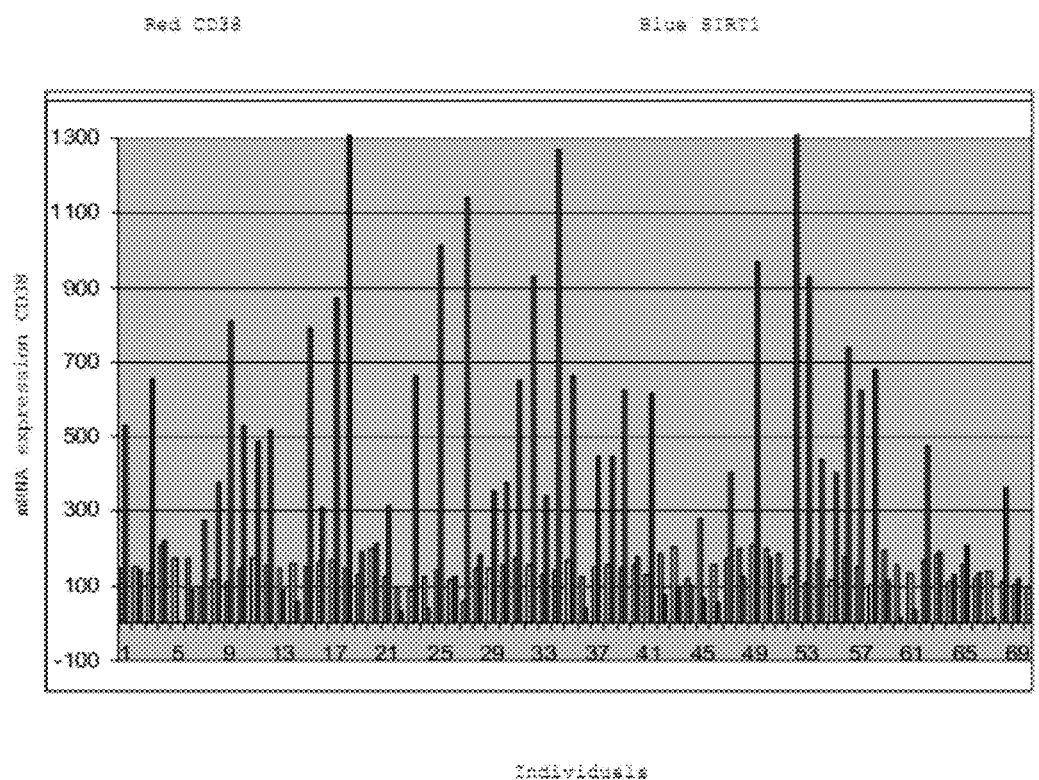

In mouse brain, liver, spleen, lung, skeletal muscle, kidney, and heart tissue, CD38 appears to be the main NADase. In the absence of CD38, the NADase activity of many of these tissues was nearly absent. In addition, CD38 was observed to be the major NADase in human cells in culture and appeared to control intracellular NAD levels (FIG. 11). Cells were screened for CD38 expression, and a correlation between mRNA, polypeptide expression, and NADase activity was observed (FIG. 11). These results indicate that CD38 is a main cellular NADase not only in mice but also in humans.

CD38 and NAD and Nicotinamide Levels

The levels of NAD and nicotinamide were observed to correlate with the expression of CD38. In these experiments, human cultured cells were used. CD38 was over-expressed, and NAD and nicotinamide levels were determined. In cells with low CD38 expression, NAD levels were high and nicotinamide levels were low.

The Effect of Metabolites of CD38 Upon the SIRT1 Activity

CD38 metabolites were tested for an effect on SIRT1 activity. Of the tested metabolites, only NAD and nicotinamide exhibited an effect on SIRT1. The other tested metabolites did not exhibit a significant effect of SIRT1 activity.

Assay for CD38 NADase Activity

Etheno-NAD was used as substrate in an assay designed to detect CD38 NADase activity. CD38 polypeptide was added in the absence or presence of 1 mM nicotinamide. The negative control was a sample lacking CD38 polypeptide. In each case, the samples were incubated for 10 minutes.

Figure 12:
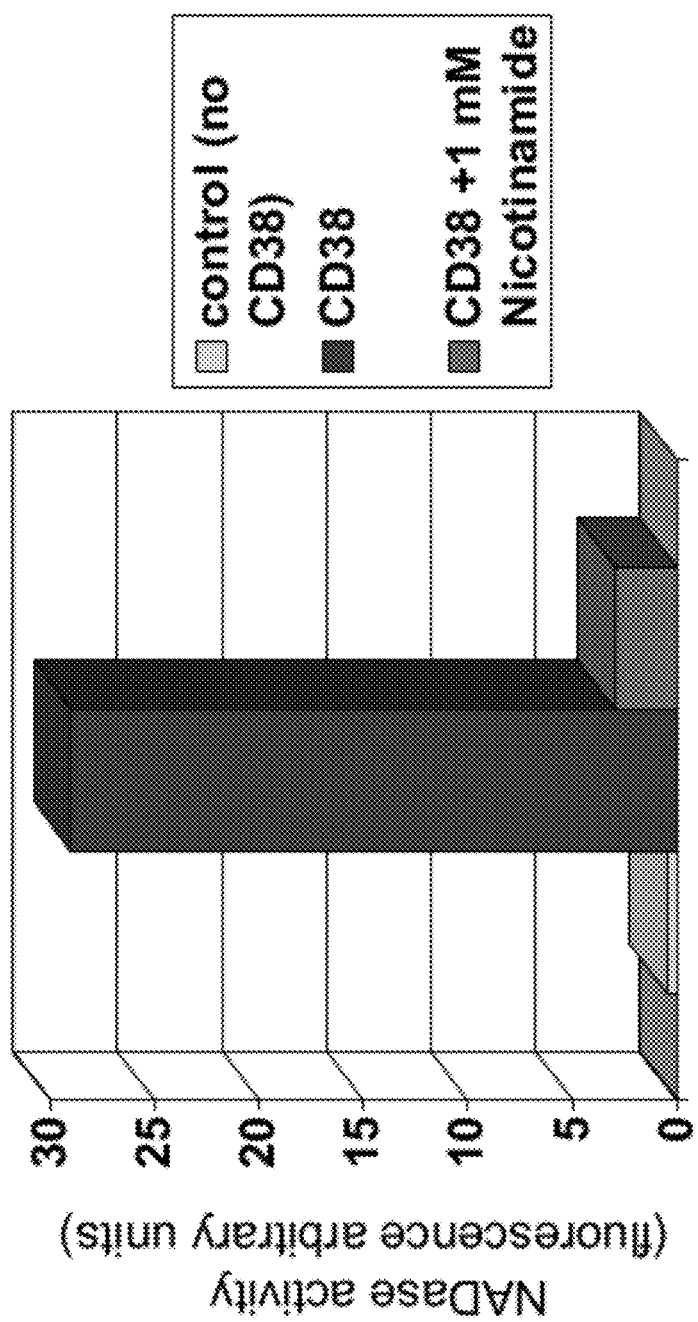
FIG. 12 is a bar graph plotting NADase activity for the indicated samples.

No CD38 NADase activity was detected in the absence of CD38 (FIG. 12). The presence of CD38 resulted in a substantial level of detectable CD38 NADase activity (FIG. 12). The presence of CD38 and 1 mM nicotinamide resulted a substantial inhibition of CD38 NADase activity (FIG. 12).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having an obesity condition, wherein said method comprises administering, to said mammal, an inhibitor of CD38, wherein said inhibitor is an anti-CD38 antibody.

2. The method of claim 1, wherein said mammal is a human.

3. The method of claim 1, wherein said inhibitor is administered to said mammal to reduce the weight of said mammal by at least 10 percent.

4. The method of claim 1, wherein said inhibitor is administered to said mammal to reduce the weight of said mammal by at least 20 percent.

5. The method of claim 1, wherein said inhibitor is administered to said mammal to reduce the weight of said mammal by at least 25 percent.

\* \* \* \* \*